United States Patent
Ding et al.

(10) Patent No.: US 9,219,885 B2
(45) Date of Patent: Dec. 22, 2015

(54) IMAGING SYSTEM WITH DEFOCUSED AND APERTURE-CROPPED LIGHT SOURCES FOR DETECTING SURFACE CHARACTERISTICS

(75) Inventors: Kexiang Ken Ding, San Diego, CA (US); Michael Anthony Laver, El Cajon, CA (US); James Frandsen, Ramona, CA (US); Samer Kabbani, Carlsbad, CA (US)

(73) Assignee: Delta Design, Inc., Poway, CA (US)

( * ) Notice: Subject to any disclaimer, the term of this patent is extended or adjusted under 35 U.S.C. 154(b) by 606 days.

(21) Appl. No.: 13/593,163

(22) Filed: Aug. 23, 2012

(65) Prior Publication Data

US 2013/0215256 A1    Aug. 22, 2013

Related U.S. Application Data

(60) Provisional application No. 61/527,036, filed on Aug. 24, 2011, provisional application No. 61/527,500, filed on Aug. 25, 2011.

(51) Int. Cl.
| | |
|---|---|
| *H04N 7/18* | (2006.01) |
| *G01N 21/88* | (2006.01) |
| *G01N 21/95* | (2006.01) |

(52) U.S. Cl.
CPC ............ *H04N 7/18* (2013.01); *G01N 21/8806* (2013.01); *G01N 21/9501* (2013.01)

(58) Field of Classification Search
CPC .. H04N 7/18; G01N 21/8806; G01N 21/9501
USPC .............. 348/86–88, 92, 125, 128, 126; 382/141–150; 356/600, 237.2–237.6
See application file for complete search history.

(56) References Cited

U.S. PATENT DOCUMENTS

| | | | | |
|---|---|---|---|---|
| 4,118,730 | A  * | 10/1978 | Lemelson | 348/94 |
| 4,207,472 | A  * | 6/1980 | Idelsohn et al. | 250/559.46 |
| 4,653,109 | A  * | 3/1987 | Lemelson et al. | 382/107 |
| 5,058,178 | A  * | 10/1991 | Ray | 382/150 |
| 5,654,977 | A  * | 8/1997 | Morris | 374/4 |
| 5,684,530 | A  * | 11/1997 | White | 348/131 |
| 5,842,060 | A  * | 11/1998 | White et al. | 396/155 |
| 6,324,298 | B1 * | 11/2001 | O'Dell et al. | 382/149 |
| 6,428,171 | B1 * | 8/2002 | Aoki et al. | 356/634 |
| 6,512,235 | B1 * | 1/2003 | Eitan et al. | 250/423 F |
| 6,522,777 | B1 * | 2/2003 | Paulsen et al. | 382/154 |
| 6,934,029 | B1 * | 8/2005 | Matzan | 356/430 |
| 7,884,947 | B2 * | 2/2011 | De Lega et al. | 356/511 |
| 2006/0114475 | A1* | 6/2006 | De Groot et al. | 356/497 |
| 2006/0291042 | A1* | 12/2006 | Alfano et al. | 359/368 |
| 2007/0147821 | A1* | 6/2007 | Gaessler et al. | 396/155 |
| 2009/0059215 | A1* | 3/2009 | Mehanian et al. | 356/237.2 |

* cited by examiner

*Primary Examiner* — Victor Kostak
(74) *Attorney, Agent, or Firm* — Foley & Lardner LLP

(57) ABSTRACT

A system for detecting characteristics of a surface includes multiple sources of lights, a platform structure configured to support the surface, a lens aligned with the platform structure, a cropping aperture, and an image receiver. The platform structure is configured to receive light from the source of light and the lens is positioned such that the source of light is not in focus, but the detected surface is in focus. The cropping aperture is configured to crop light reflected from the surface, and the image receiver is configured to receive the light conditioned by the cropping aperture.

30 Claims, 16 Drawing Sheets

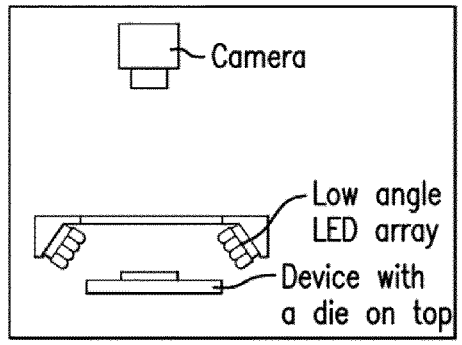 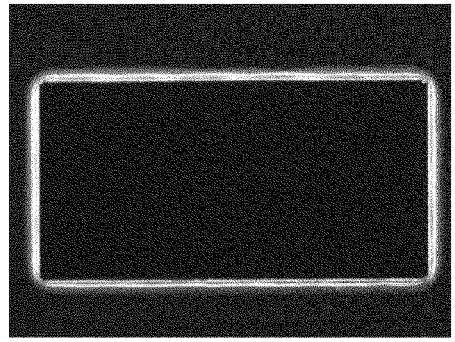
FIG.2A                FIG.2B
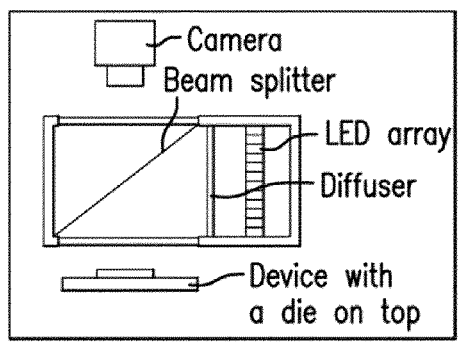 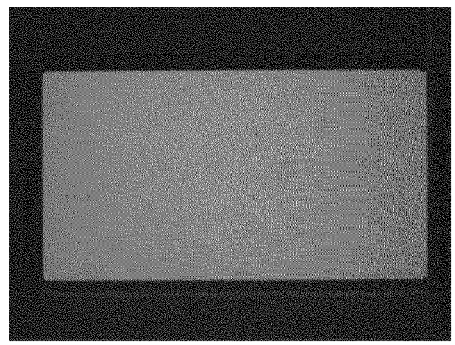
FIG.3A                FIG.3B
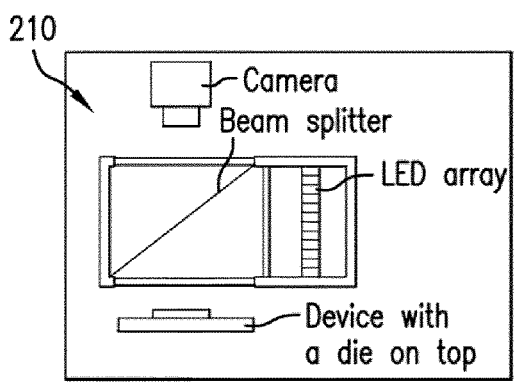 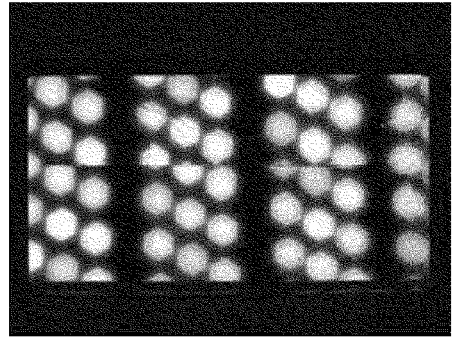
FIG.4A                FIG.4B In-Pocket Out-of-Pocket

IMAGING SYSTEM WITH DEFOCUSED AND APERTURE-CROPPED LIGHT SOURCES FOR DETECTING SURFACE CHARACTERISTICS

CROSS-REFERENCE TO RELATED APPLICATIONS

This application claims priority to and the benefit of U.S. Provisional Patent Application Nos. 61/527,036, filed Aug. 24, 2011, and 61/527,500, filed Aug. 25, 2011, both of which are incorporated by reference in their entireties.

BACKGROUND

The present disclosure relates to an imaging system for detecting characteristics of a surface. Such characteristics may include cracks, micro-recesses, warping, pits, bulges, tilting, etc. In some embodiments of the present technology, the imaging system is particularly configured to inspect characteristics of the surface of a flat panel, a die, or a bare wafer for an integrated-circuit.

Very faint micro-cracks, flatness, and tilt angle are examples characteristics associated with the surface of a bare wafer, a die, or a flat panel that may be difficult to detect using standard or high-resolution cameras and regular dark-field or bright-field lighting.

SUMMARY

An imaging system uses multiple sources of light positioned at a relatively large distance from the surface to be detected. The light sources are arranged in an array, defocused (i.e., purposefully out-of-focused), and aperture-cropped to detect the surface characteristics. In some embodiments, the imaging system uses the multiple sources of light to indirectly detect surface characteristics on a wafer, a die, or a flat panel, where such characteristics may include cracks, flatness, and tilt angle among other characteristics. The characteristics are indirectly detected by analyzing and recognizing size, shape, and position changes of light reflected off of the surface by each individual light source.

Individual light spots on the resulting image are compared to a learned reference image to identify differences to with respect to size, shape, and position between the spots and the reference spots, which are symptomatic of irregularities on the surface being inspected. According to an exemplary embodiment, surface cracks, flatness, and tilt angle on a wafer, a die, or a flat panel surface can be readily detected without using a high-resolution camera because the changes in the light spots are highlighted and magnified by a relatively large distance between the light source and the reflecting surface in the imaging system.

While techniques and imaging systems disclosed herein may be particularly useful for efficient, non-destructive testing of wafers for integrated circuits, the techniques and imaging systems may apply to any reflective or partially-reflective surface for detection of cracking, flatness, tilt angle, and/or other characteristics of a surface, and may also be useful for identification of sub-surface characteristics for translucent substrates or substrates that manifest indicators of sub-surface characteristics on surfaces thereof.

One embodiment of the invention relates to a system for detecting characteristics of a surface. The system includes multiple sources of light, a platform structure configured to hold the surface, a lens aligned with the platform structure, a cropping aperture, and an image receiver. The platform structure is configured to receive light from the sources of light and the lens is positioned such that the detected surface is in focus, but the sources of light are not in focus. The cropping aperture is configured to crop light reflected from the surface, and the image receiver is configured to receive the light conditioned by the cropping aperture.

Another embodiment of the invention relates to a method for detecting characteristics of a reflective surface. The method includes a step of directing light, for example spots of light, from multiple sources of light to the surface, where the sources of light includes an array of lights. The method further includes steps of focusing a lens on the surface for receiving light reflected from the surface and cropping the light received from the surface. Additionally, the method includes a step of examining an image produced from the cropped light for irregularities in light, for example spots of light, associated with the sources of light, wherein the irregularities correspond to characteristics of the surface.

Yet another embodiment of the invention relates to a method of using an imaging system to inspect a surface for cracks, warping, and tilting. The method includes recording size, shape, and position of light spots reflected from a reference surface and a surface to be inspected. The method further includes comparing the size, shape, and position of light spots reflected from the surface to be inspected with those of the reference surface.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, in which:

FIG. 2A is a schematic view of an imaging system configured for crack detection using dark-field lighting.

FIG. 2B is a digital image of a cracked surface illuminated via the imaging system of FIG. 2A.

FIG. 3A is a schematic view of an imaging system configured for crack detection using bright-field lighting with a diffuser.

FIG. 3B is a digital image of a cracked surface illuminated via the imaging system of FIG. 3A.

FIG. 4A is a schematic view of an imaging system configured for crack detection using multiple light-emitting diode light sources according to an exemplary embodiment of the invention.

FIG. 4B is a digital image of a cracked surface illuminated via the imaging system of FIG. 4A

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
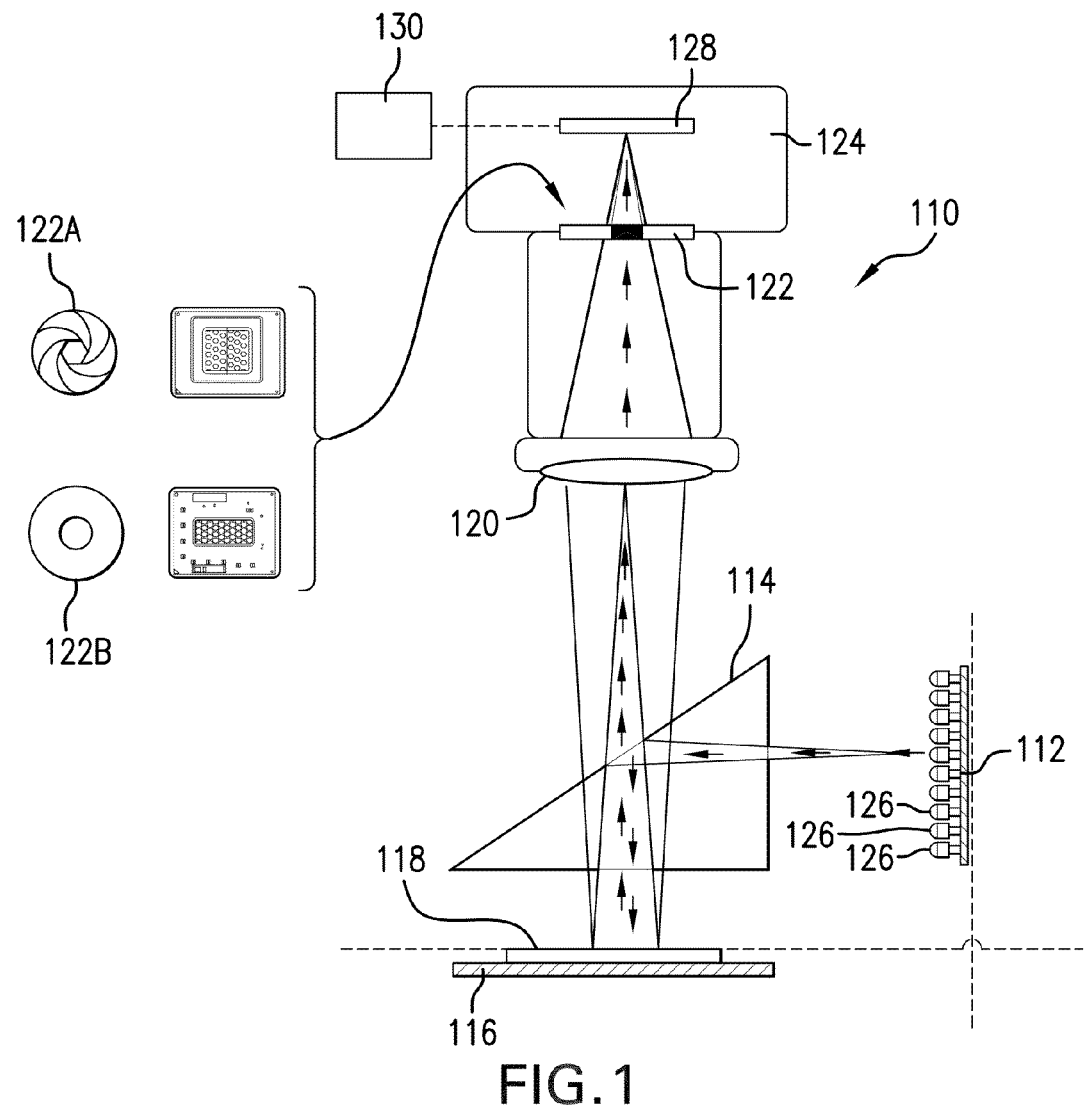
FIG. 1 is schematic view of an imaging system according to an exemplary embodiment of the invention.

Referring to FIG. 1, an imaging system 110 includes multiple sources of light 112, a beam splitter 114, a platform structure 116 supporting a surface 118 to be examined, a lens 120, an aperture 122 (e.g., cropping aperture), and an image receiver 124 (e.g., camera). Apertures 122A and 122B show opening shapes of alternate embodiments of the cropping apertures.

In this embodiment, the sources of light 112 includes an array of light emitting devices (e.g., plurality of light sources). The sources of light 112 may include a grid or panel of light-emitting diodes 126. In other embodiments, the sources of light 112 may include small light bulbs, fluorescent lights, etc. The sources of light 112 may be identical to one another, or different colors, different intensities, different shapes (e.g. round, annular), different positions, etc. The sources of light 112 may be moveable or fixed relative to one another. The sources of light 112 may be wired in series or in parallel. In some contemplated embodiments, only a single source of light is used, where the light source is split or refracted to provide a continuous or discontinuous light spots directed to the surface and to be reflected from the surface.

In this embodiment, the beam splitter 114 is essentially a partial mirror, reflecting some of the light from the source of light 112 toward the surface 118 to be examined, while allowing other light to pass through the beam splitter 114. The distance and relative orientation between the source of light 112 and the beam splitter 114 may be adjusted depending upon the particular setup of the imaging system 110. In some embodiments, the beam splitter 114 is flat and has a uniform thickness. In other embodiments, the beam splitter 114 is concave, convex, prismatic, or otherwise configured to augment the direction or character of the light from the source 112 or the light reflected from the surface 118 to be examined.

In this embodiment, the platform structure 116 is configured to support the surface 118 to be examined and configured to interlock the surface 118 to be examined. The platform structure 116 may be configured to be precisely controlled to move in one or more translational or rotational degrees of freedom (e.g., single-axis actuator table or slide). Similarly, the source of light 112 may be mounted to an adjustable platform structure configured to be precisely controlled by solenoid, screw-drive linear actuator, etc. Additionally, the platform structure 118 may include vibration-control elements configured to dampen external vibrations from reaching the surface 118 to be examined.

The surface 118 to be examined may include a bare wafer, a die, a flat panel, or another surface that is at least partially reflective. The surface 118 may or may not be flat, continuous, or uniform in material composition. However, in some particular intended applications of the disclosed technology, the surface 118 is a bare wafer for use with an integrated circuit.

According to an exemplary embodiment, the lens 120 is configured to receive light reflected from the surface 118 to be examined. The lens 120 may be a convex, camera lens or another type of lens. In contemplated embodiments, the lens 120 may be integrated with or fixed relative to the beam splitter 114.

According to an exemplary embodiment, the imaging system 110 includes the aperture 122. In some embodiments, the aperture 122B is a circular cropping aperture, as opposed to conventional polygonal apertures 122A commonly used in cameras. In other embodiments, the aperture is annular or otherwise shaped. In still other embodiments, the aperture is polygonal, such as twenty-sided regular polygon.

According to an exemplary embodiment, the image receiver 124 may be or include an image recording device 128 (e.g., digital camera, recorder), an image processing device (e.g., optical sensors coupled to a computer 130), and/or a human observer. In some embodiments, the image recording device 128 includes a charge-coupled device (CCD) of a digital camera. However, in other embodiments, the image recording 128 device may include another type of recording media. In still other contemplated embodiments, the image receiver 124 may be coupled to a computer 130 to process or analyze aspects of the image with or without recording the image. In some embodiments, a human may view the image through the lens 120 to identify characteristics of the surface 118 based upon visual inspection of light reflected from the surface 118.

Still referring to FIG. 1, during use of the imaging system 110, light from the source 112 is redirected orthogonally toward the surface 118 by the beam splitter 114. The light is then reflected vertically from the surface 118 and passes back to and through the beam splitter 114 to the lens 120. The lens 120 directs the light through the cropping aperture 122 after which the light is received by the image receiver 124. Accordingly, the optical axis of the image receiver 124 (e.g., camera) to view the surface 118 is co-axial with the light axis of the beam splitter 114. When the optical axis is coaxial to the light axis, as in FIG. 1, multiple light sources 126 project individual shapes on the image receiver 124 (e.g., camera CCD image) from the surface 118. When the surface 118 is the focused plane, the multiple light sources 126 are defocused.

Cracks, distortions, or tilting of the surface 118 at least partially change the reflective angles of the surface 118. As a result, the reflections of individual light sources 126 are influenced by surface defects, changing the size, shape, and/or position of the reflected light sources that are projected to the image receiver 124. These changes indicate the surface 118 has an abnormality, the magnitude of which is related to the observed changes in the light spots shapes.

In other embodiments, mirrors, lenses, filters, and other optical tools may be used to otherwise direct or condition the light. In some contemplated embodiments, the image provided by light reflected from the surface 118 is distorted in a known way that is recognized and accounted for when processing the image for additional or other types of distortions that may correspond to irregularities in the surface. As such, in some contemplated embodiments, the image receiver 124, the beam splitter 114, and the surface 118 may not be co-linear, and/or the light source 112 may not be orthogonal thereto.

I. Crack Detection

Referring to FIGS. 2A, 2B, 3A, and 3B, cracks on a reflective surface may be very difficult to detect using dark-field (FIGS. 2A and 2B) or bright-field lighting, where the light has been diffused (FIGS. 3A and 3B).

Referring now to FIGS. 4A and 4B, using an imaging system 210 having features in common with the imaging system 110 as shown in FIG. 1, the small angle difference caused by a crack changing the reflective angle of adjoining surface fragments in turn causes significant change to the reflected light size, shape, and position relative to other light spots when viewed at a relatively large distance from the surface fragments, as discussed below with regard to FIG. 9. Furthermore, crack lines are highlighted indirectly due to the spot shape distortions. In the case of round spots reflected off of the cracked surface from an array of light-emitting diodes, the peripheries of the spots adjoining the crack are no longer round.

Figure 5A:
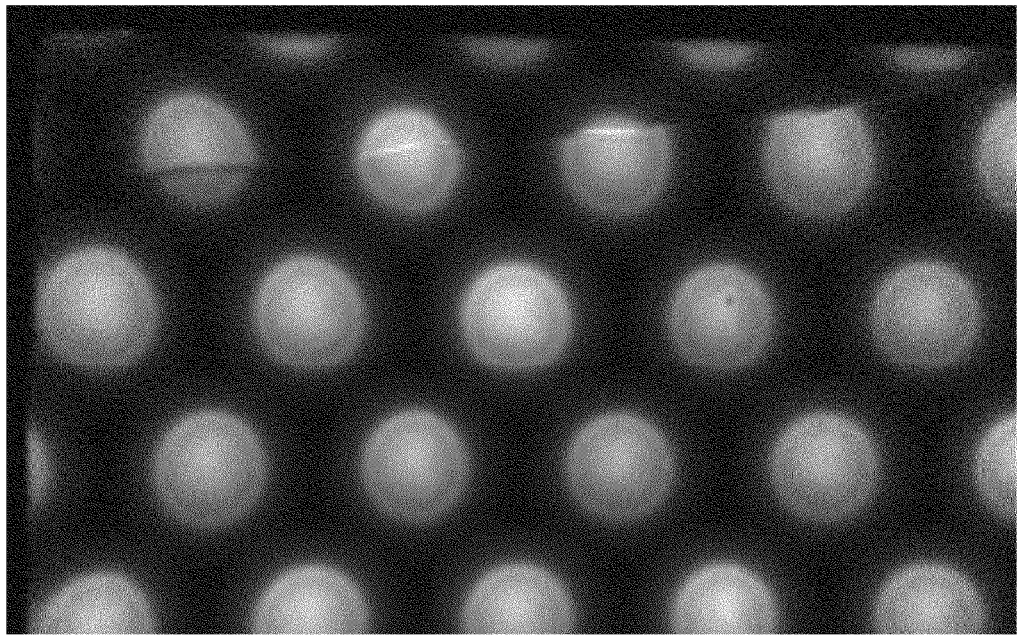
FIG. 5A is a digital image of a cracked die with the focus plane on the die as opposed to the light sources.
Figure 5B:
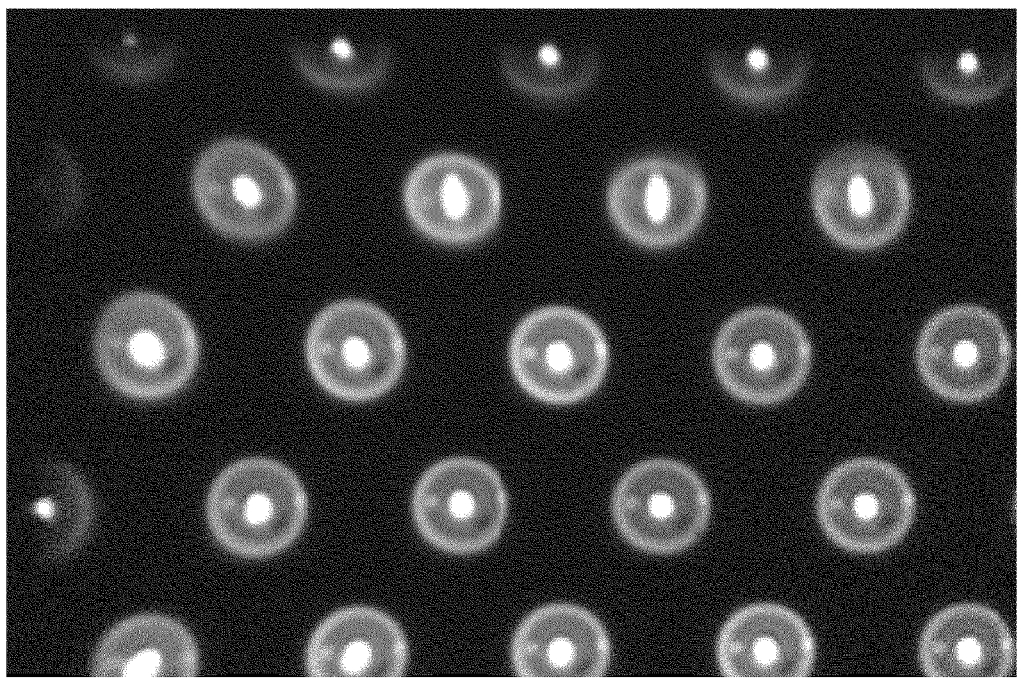
FIG. 5B is a digital image of a cracked die with the focus plane on the light sources as opposed to the die.

In this embodiment, a light-emitting diode array is used as the light source. In other embodiments, the imaging system uses other arrays of light sources. The lens focuses the image receiver (e.g., camera) on the surface (e.g., surface plane of the bare die), and accordingly the image receiver is defocused on the plane of the light source. Cracks are indirectly shown in the distortions of the reflected light spots in the resulting image, as shown in FIG. 5A. By contrast, if the lens is focused on the plane of the light source and the reflective surface is defocused, cracks may not be as clearly visible, as shown in FIG. 5B.

II. Flatness Detection

Flatness may be an important characteristic of a wafer for automation handling equipment. Embodiments of the imaging system 110 of FIG. 1, using multiple light sources that are defocused, may be used to inspect the flatness of the wafer or other surfaces. Inspection and confidence in the flatness of a wafer may be important before picking up and processing the wafer. According to an exemplary embodiment, before inspection, a known flat wafer or other surface may be used as a reference for establishing desired light spots of reflected light (i.e., training a computerized image processor). Use of a reference establishes the baseline light spots for comparison.

Figure 6:
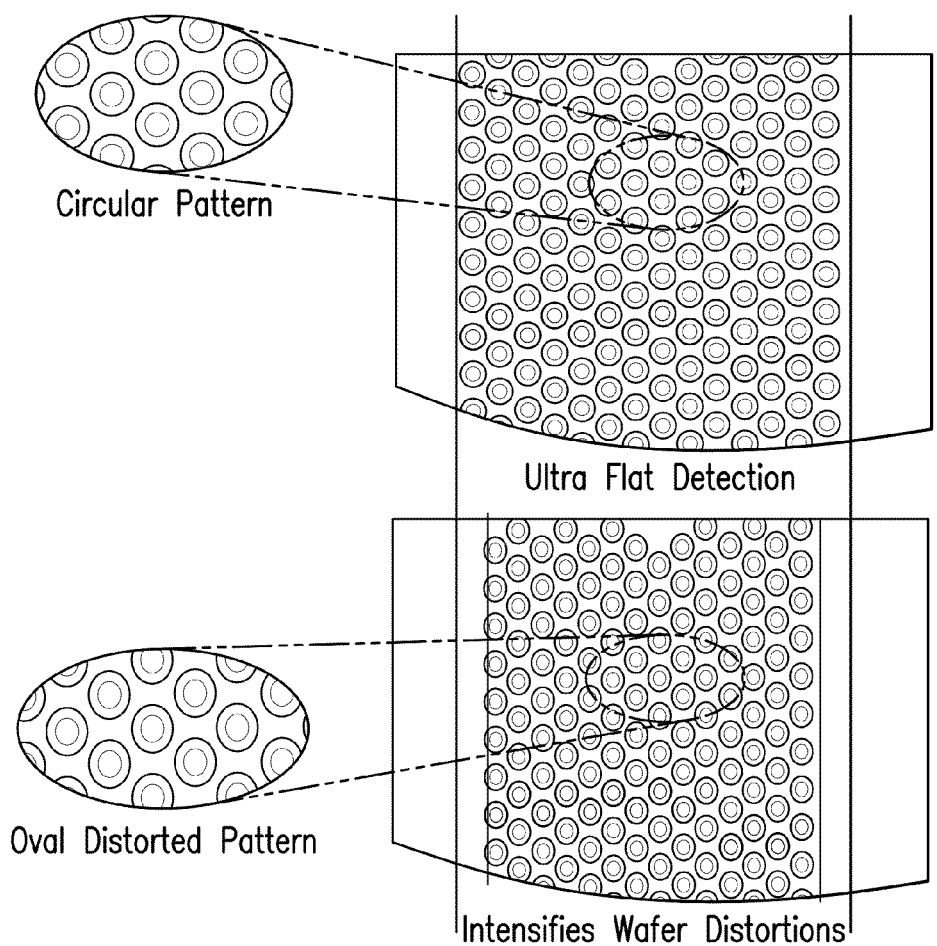
FIG. 6 includes images of light reflected from a flat wafer surface (above) and a warped wafer surface (below), with expanded portions thereof.

Referring to FIG. 6, for a non-flat wafer or other surface, the light spots of reflected light (lower image) are distorted relative to the reference light spots (upper image). Furthermore, because the light plane is relatively far from the surface that is reflecting the light, any small angle changes associated with warping (i.e., flatness error) on the surface are magnified by the long optical distance, making image processing easier without costly high-resolution cameras, etc.

To identify warping, the image receiver is focused on the surface plane of the wafer and defocused on the light source plane. Indicia of flatness error can be seen as differences in the light spots produced by the surface being inspected relative to the baseline light spots. The degree of warping may be quantified by comparing the amount of distortion relative to the reference light spots, or a scale of known distortions and associated warping.

III. Tilt Detection

Figure 7:
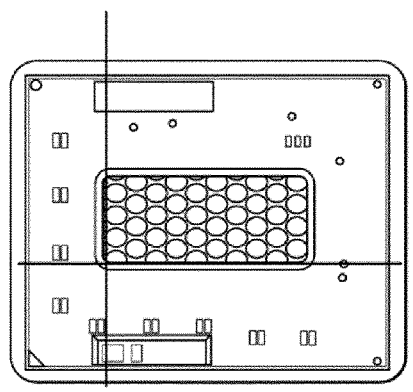
FIG. 7 includes images of light reflected from an in-pocket device (above) and an out-of-pocket or tilted device (below).
Figure 7:
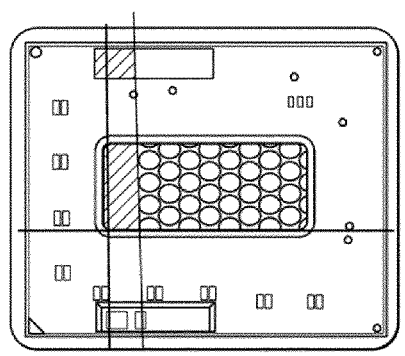

Identification of tilting of a surface be useful. Tilting may indicate that a device is not properly seated in an associated pocket, which may be an issue for device handling and processing. According to an exemplary embodiment, the imaging system 110 of FIG. 1 may be used for detection of tilting. A known, properly-seated device (e.g., surface to be tested, wafer, die, flat panel, etc.) may be used to establish the reference light spots of reflected light, as shown in FIG. 7 (upper image). Subsequently, during inspection of another device (e.g., runtime), if the other device is out of the pocket, the resulting light spot locations may shift as shown in FIG. 7 (lower image).

IV. Method of Testing by Comparison to Reference

According to an exemplary embodiment, an imaging system may be used to test characteristics of a surface using reflected light that is defocused and aperture-cropped from multiple sources, and comparing the results with the reference in size, shape and position.

To establish a reference in size, shape and position, an operator should record them of reflected light provided by a known, correct surface at regular light intensities. The operator should find each light spot on the image. The operator should then determine the size, shape, and position of each light spot relative to one another and with respect to a fixed frame. The operator should further save the size, shape, and position.

During runtime inspections of additional surfaces to be examined, the operator should upload the size, shape, and position associated with the known, correct surface. The operator should then align the current light spots with the light spots of the reference. The operator should then determine the size, shape, and position of each light spot reflected by the surface being inspected and should compare the size, shape, and position with the recorded reference to detect differences, which may be indicative of surface cracks, warping, and/or tilting.

V. Various Exemplary Embodiments

Figure 8A:
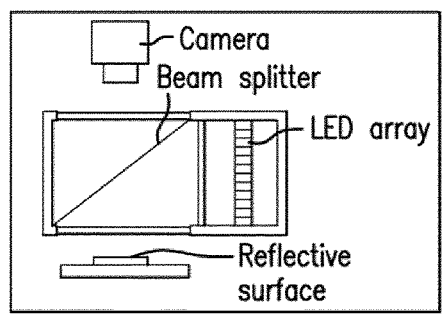
FIG. 8A is a schematic view of the imaging system of FIG. 4A.
Figure 8B:
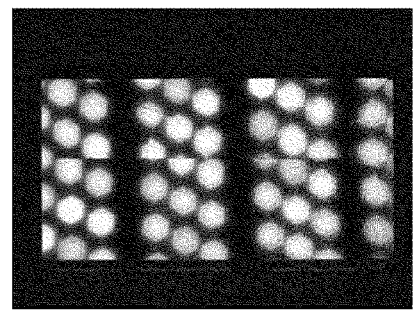
FIG. 8B is a digital image of the cracked surface of FIG. 4B.

Referring to FIG. 8, a two-dimensional lighting spots on the camera image (FIG. 8B) is provided by reflection of multiple light sources on a cracked surface. In this application, the two-dimensional light sources include light-emitting diodes arranged in an array of light spots. Individual lights in the array may be turned on or off, or brightened or dulled to identify the particular source of lights shown in the reflected light spots. To reduce the optical distortions, the optical axis of the camera shown in FIG. 8 is coaxial with the optical axis of the light that is reflected on the surface. Furthermore, a beam splitter is used to facilitate the co-axial illumination.

Figure 9:
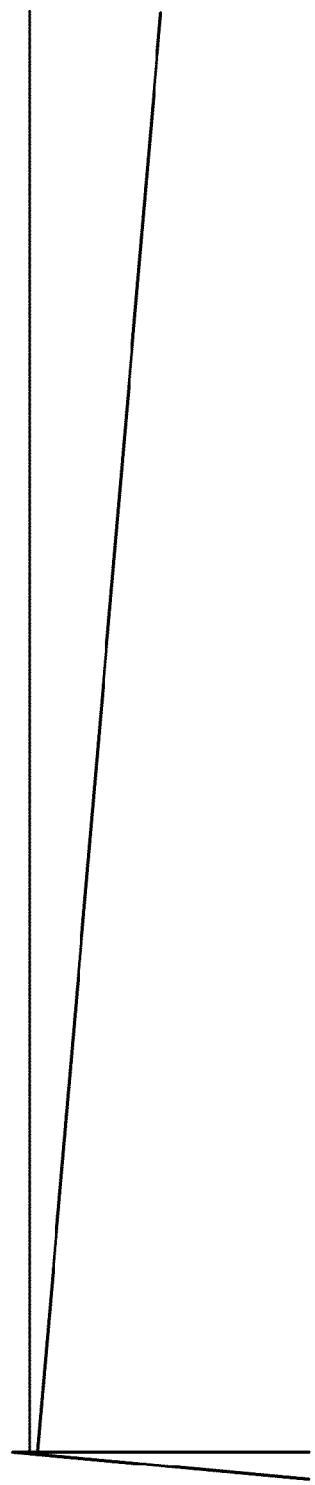
FIG. 9 is a diagram comparing separations between ends of arms of an angle at distances relatively far from and close to the vertex, which relates to amplification by the imaging system of characteristics of the surface.

According to a preferred embodiment, the image receiver is located a relatively large distance away from the reflective surface, as illustrated in FIG. 9, to magnify the influence of the surface crack, flatness, and tilt-angle, etc., on the resulting light spots of reflected lights. In some embodiments, the relatively large distance may be between 1 and 100 times the longest dimension of the surface to be examined. In some embodiments, the relatively large distance may be 1 to 100 times the distance from the source of light to the surface to be examined. In some embodiments, the relatively large distance may be at least an inch, at least six inches, at least a foot, at least two feet, more than two feet, or less than inch. However, the separation distance may be limited by the physical dimension of the equipment, lens aperture, light spot size, etc.

Still referring to FIG. 9, the distance from the light source (e.g., light-emitting diode array) to the surface to be inspected (e.g., piece that may be cracked) is large relative to the size of the surface to be inspected. In some embodiments, the distance is about ten times greater than the length, width, or height of the surface to be inspected. In some embodiments, the distance is greater than the longest dimension of the surface to be inspected, greater than five times the greatest dimension, greater than twenty times the greatest dimension, or less than the greatest dimension. In some embodiments, the distance from the light source to the surface to be inspected is less than the distance from the surface to be inspected to the image receiver, such as less than half, less than a quarter, less than a tenth. But in other embodiments, the distance from the light source to the surface to be inspected is greater than the distance from the surface to be inspected to the image receiver. The separation distance may be limited by the physical dimension of the equipment, lens aperture, light spot size, etc.

Figure 10:
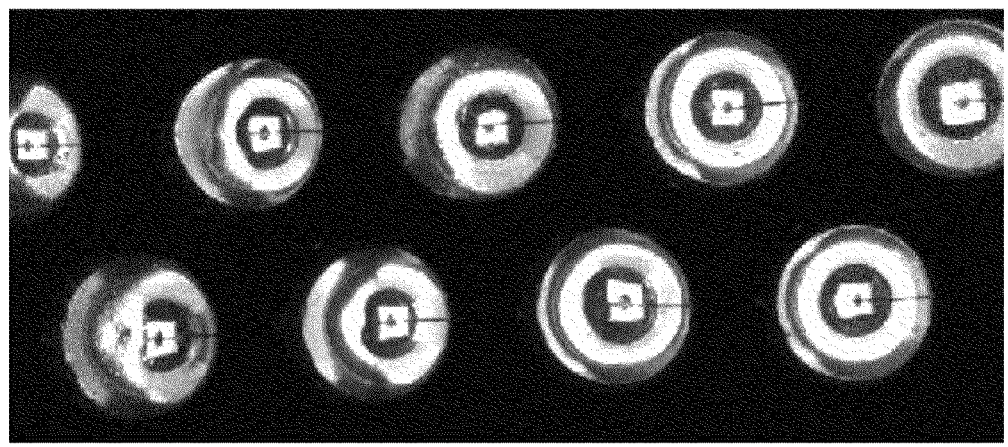
FIG. 10 is a digital image of a reflection of light-emitting diodes on a surface with the imaging system focused on the light-emitting diodes.
Figure 11:
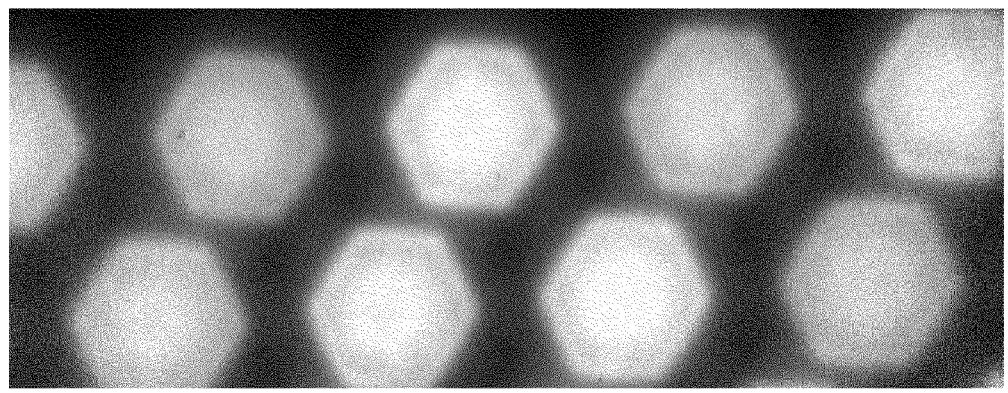
FIG. 11 is a digital image of a reflection of light-emitting diodes on a surface with the imaging system defocused on the light-emitting diodes and focused on the detected surface.
Figure 12:
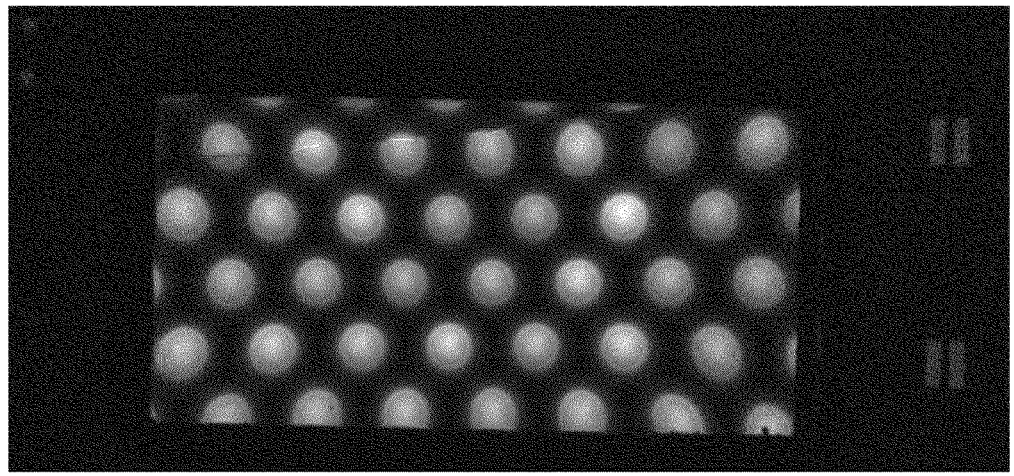
FIG. 12 is a digital image of a reflection of light-emitting diodes on a cracked surface with the imaging system focused on the surface and defocused on the lights.
Figure 13:
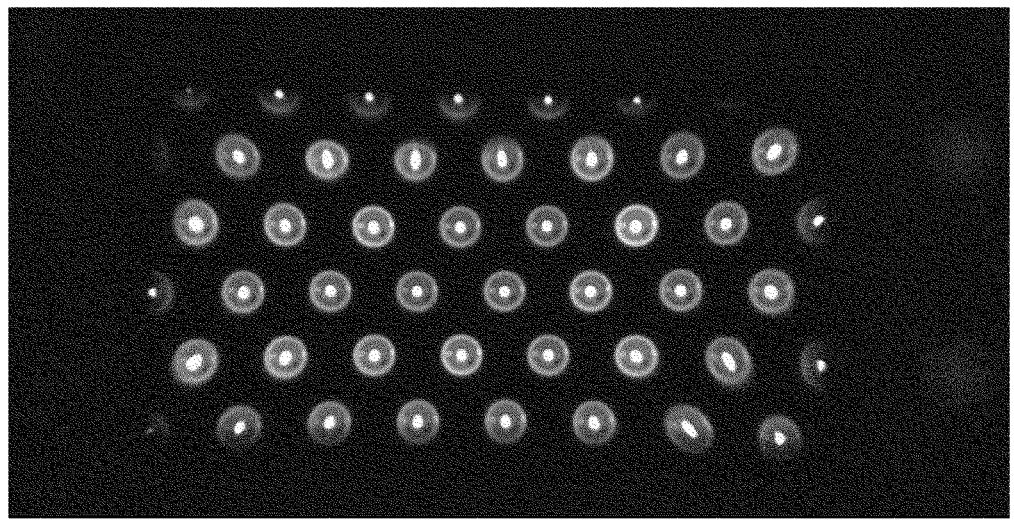
FIG. 13 is a digital image of a reflection of light-emitting diodes on the cracked surface of FIG. 12 with the imaging system focused on the light-emitting diodes.

Referring to FIG. 10, if the imaging system focuses on the source of the light (i.e., light plane), then the structures producing the light (e.g., light-emitting diode, filament of bulb, etc.) are clear in the resulting image. Particular structures of the source of light may complicate image processing, as shown in FIG. 10, by hiding aspects of the image indicative of a crack, warp, tilt, etc. Instead, according to an exemplary embodiment, the light plane is purposely defocused (i.e., actively put out of focus) in order to make each light spot appear in a smooth gray scale. FIG. 11, when compared to FIG. 10, demonstrates that a defocused light plane has a more uniform intensity, which is believed to make each light spot more efficient for image processing and detection of surface irregularities. Accordingly, if the surface being inspected is focused, in turn defocusing the light plane, then surface cracks are visible or more readily detectible, as shown in FIG. 12 (crack passing through upper row of spots) and contrasted with FIG. 13 (obscuring same crack).

Figure 14:
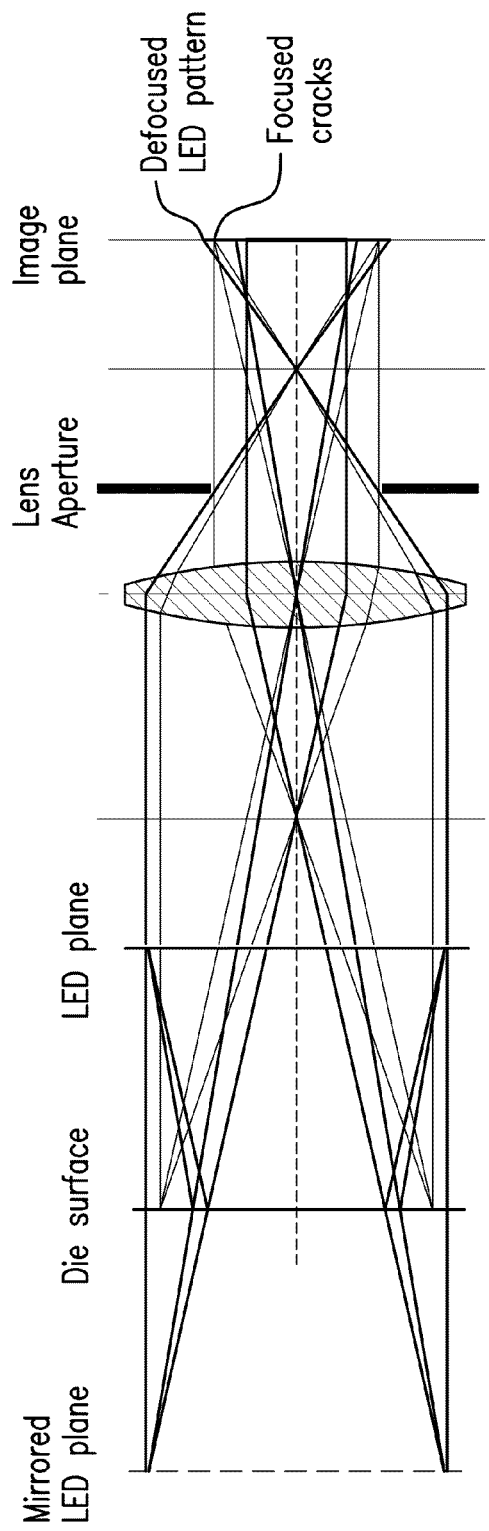
FIG. 14 is a schematic diagram illustrating focused and defocused image planes with respect to the light source.
Figure 15A:
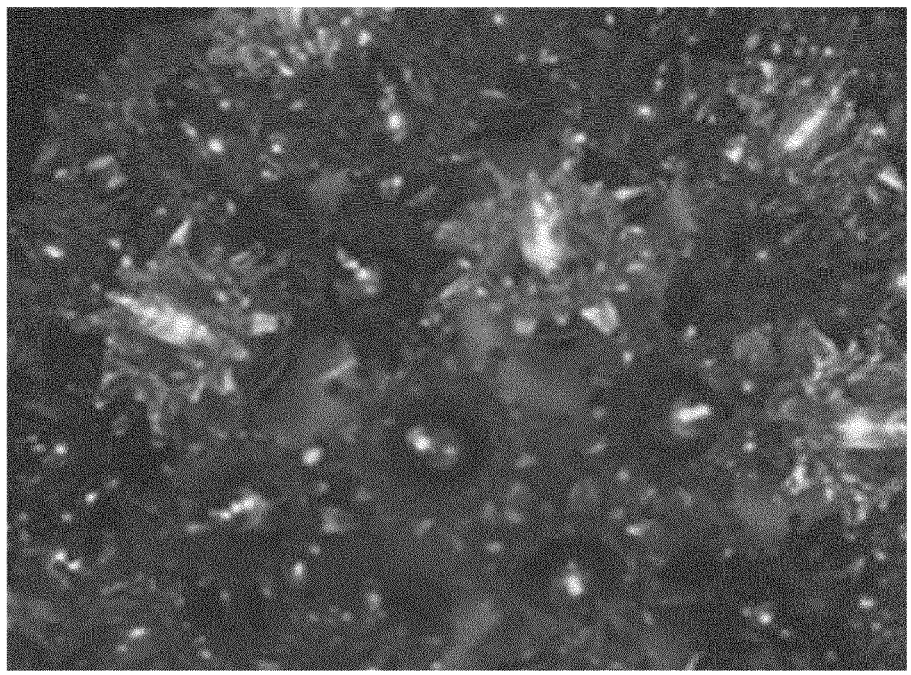
FIG. 15A is a digital image of a reflection of light spots on a surface with the imaging system focused on the source of the light spots.
Figure 15B:
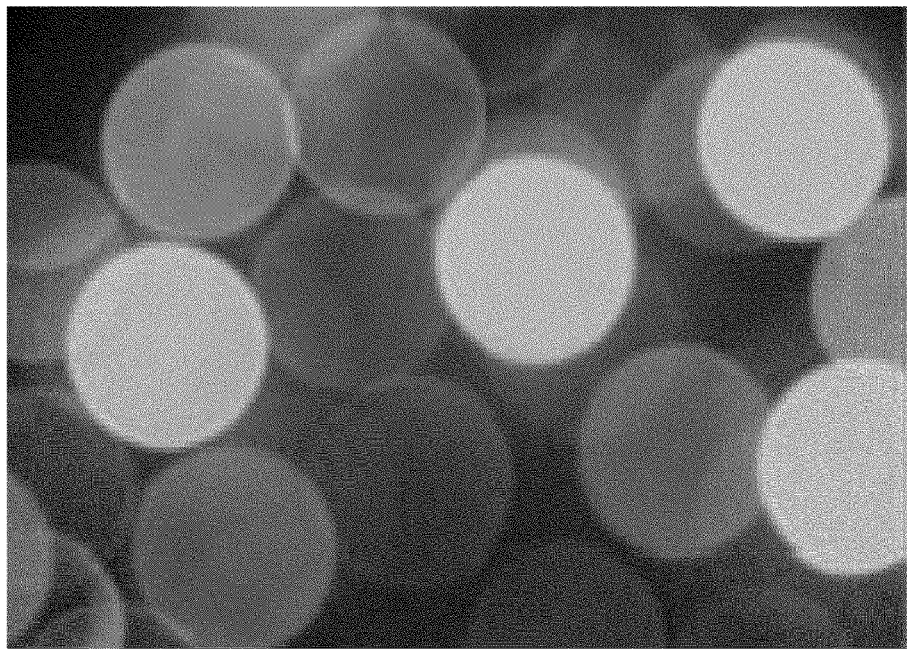
FIG. 15B is a digital image of a reflection of the light spots of FIG. 15 on the surface with the imaging system defocused on the sources of the light spots.

Referring now to FIG. 14, embodiments of the imaging system include defocused, as opposed to focused, arrays of multiple light sources. For the focused plane, each point on the plane corresponds to one point on the reflected image. For the defocused plane, each point on the plane corresponds to a spot area on the image. Accordingly, if the defocused plane does not have distinct light sources (e.g., light points), but instead uses diffused light or a single source, the reflected image may be blurred in some embodiments (FIG. 15B). Additionally, if the image plane has concentrated points of light, then the points of light on the resulting image will dominate (FIG. 15A), hiding features of interest, such as cracks.

Figure 16:
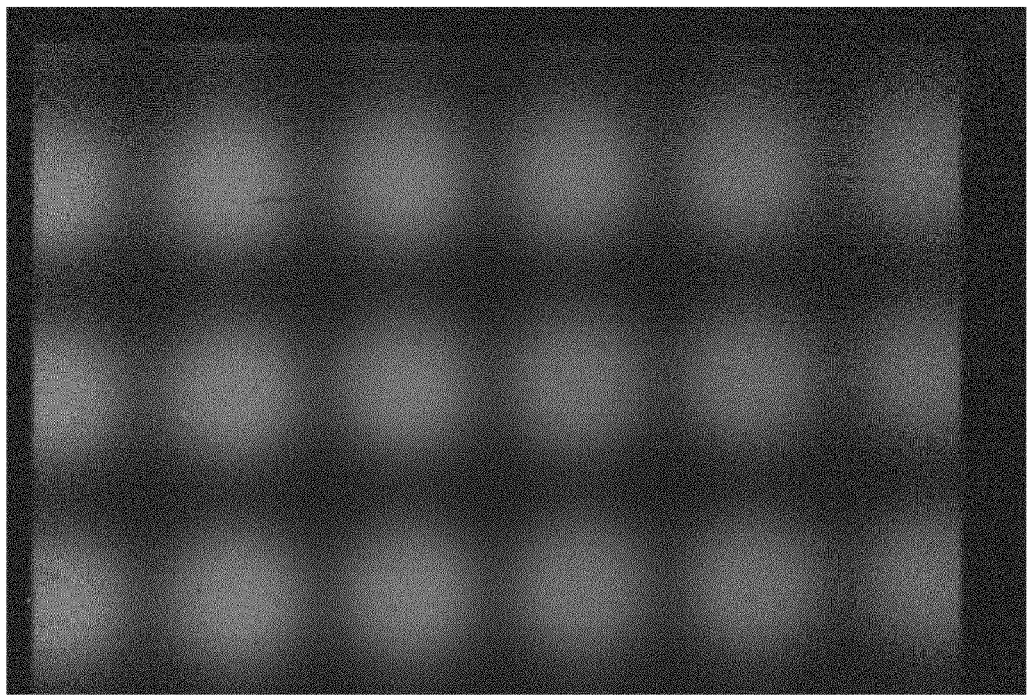
FIG. 16 is a digital image of defocused light spots without aperture cropping.

Defocused light spots in general may have blurry edges, as shown in FIG. 16. Such blurry edges may increase the difficulty of image processing. However, to overcome such difficulties, Applicants have found that a lens aperture may be used to control the light spot edges and shapes, which may allow for defocused light spots with sharp edges.

Figure 17:
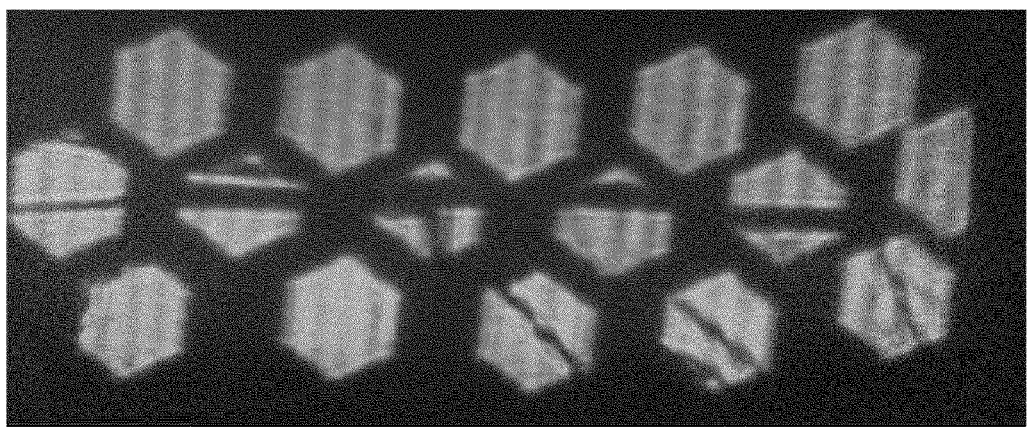
FIG. 17 is a digital image of defocused light spots with hexagonal aperture cropping.
Figure 18:
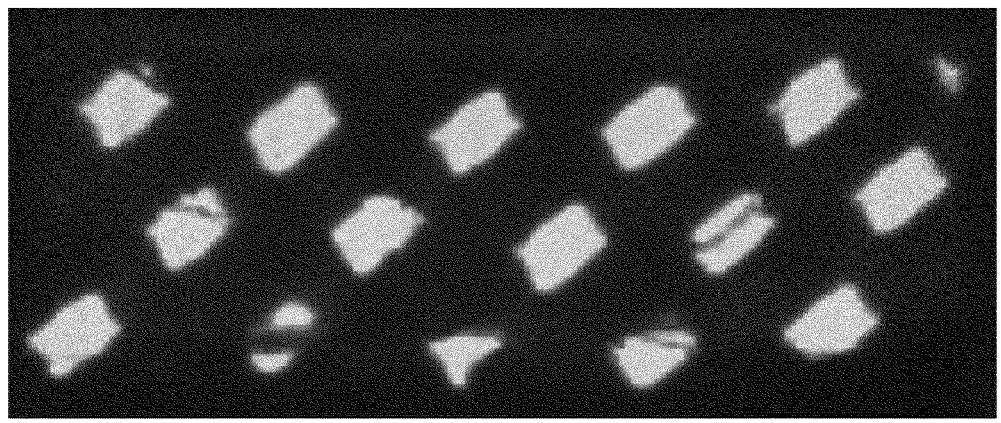
FIG. 18 is a digital image of defocused light spots with rectangular aperture cropping.
Figure 19:
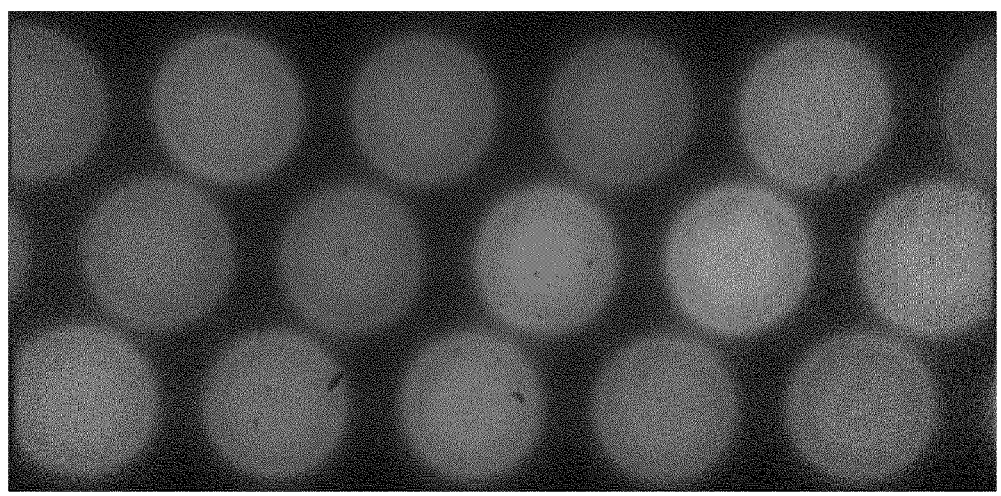
FIG. 19 is a digital image of defocused light spots with circular aperture cropping.

Still referring to FIG. 17, hexagon shapes are produced by the lens aperture, which has a hexagonal opening. The hexagon shapes are visible only on the projected image of the camera, as opposed to being produced by the source of light. If the aperture is rectangular, the reflected light spots will have rectangle shapes (FIG. 18). Applicants have found that a circular shape may appear if the aperture is round (FIG. 19). While only one aperture is typically used per camera, all light spots on the resulting image are cropped with the shape of the aperture.

Figure 20A:
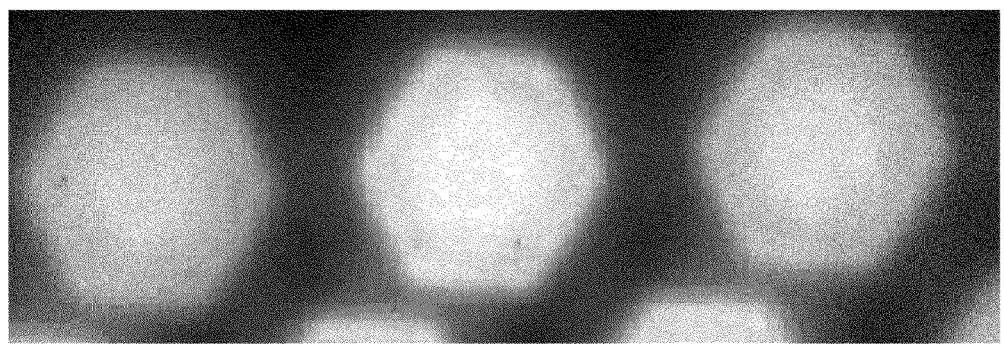
FIG. 20A is a digital image of defocused light spots with hexagonal aperture cropping where the image is in a first orientation.
Figure 20B:
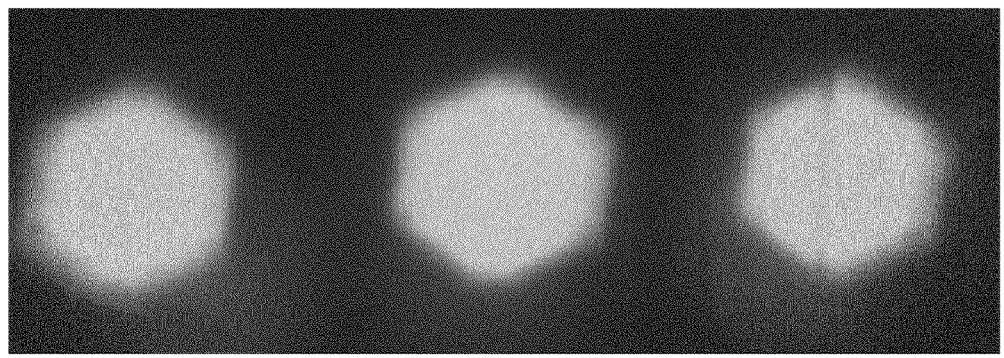
FIG. 20B is a digital image of defocused light spots of FIG. 20A in a second orientation.

Applicants believe that most lens apertures are polygonal in shape, however in some embodiments a circular cropping aperture is preferred. With polygonal apertures, after adjusting the focus of the imaging system, the rotation angle of polygons in the resulting image may be random or difficult to consistently control, as shown in FIG. 18 with the rectangular shapes. Accordingly, variation in image spot orientation (compare orientation of hexagonal spots in FIG. 20A with those of FIG. 20B) may complicate processing of the image for detection of variations in image spot shape that indicate cracks or other irregularities. However, Applicants have found that a circularly shaped cropping aperture simplifies the process of shape detection for identification of cracks or other irregularities because circular spots appear identically circular regardless of orientation.

Figure 21B:
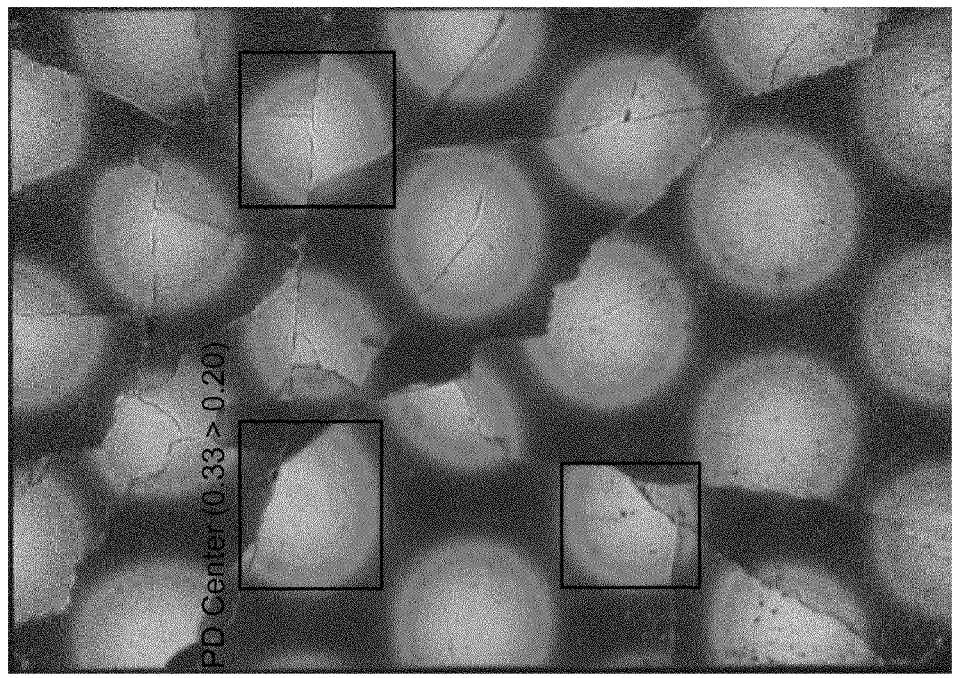
FIG. 21B is a digital image of a reflection from a cracked surface.
Figure 21A:
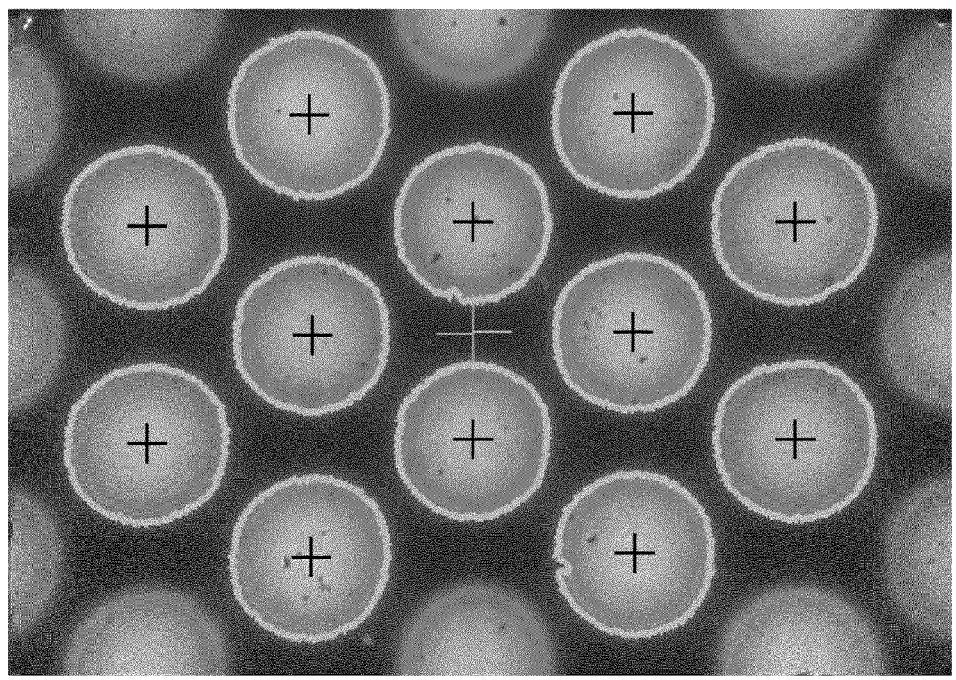
FIG. 21A is a digital image of a reflection from a reference surface.

Referring to FIGS. 21A and 21B, the surface crack, tilt, warp, and/or other distortions may be detected by comparing reflected light spots produced by the runtime size, shape and position with those of the trained reference. To identify cracks, tilting, and warping, etc., the size, location, and shape of each reflected light spot in the image may be compared. To perform the comparison, the light spots in the inspected region should be identified with respect to the same region in the reference light spots. However, the light spots locations may differ with multiple devices on a tray or a pocket plate. Furthermore, if the inspected surface is cracked, tilted, or distorted, the imaged light spots may be greatly distorted and hard to recognize. In some embodiments, the control algorithms may also separately identify the distortions caused by the crack, tilt, and flatness errors from those distortions associated with the lens or other factors.

According to an exemplary embodiment, a control algorithm for the imaging system includes a multiple-object light spots locator. The light spot locator locates and identifies corresponding reference light spots despite distortion caused by cracking, tilting, warping, etc. To locate and identify the corresponding light spots position, in some embodiments the operator or the control computer turns some lights on or off, or dimmer or brighter. In some such embodiments, the operator or the control computer may also move lights closer or farther from the inspected surface, or from one another. Accordingly, control hardware and/or software function to control individual light sources of the array of multiple light sources. The light spots, in some embodiments, are generated with light sources having two dimensional features.

Figure 22A:
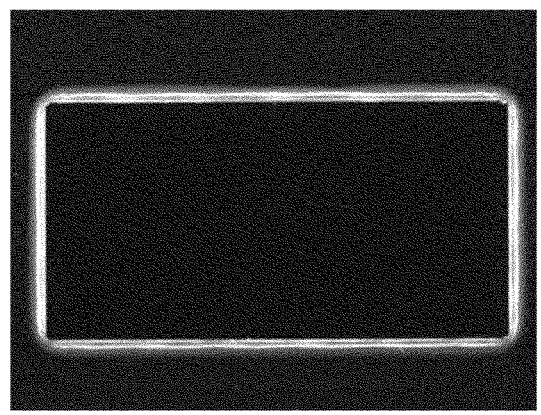
FIG. 22A is a digital image of a cracked surface illuminated via the imaging system using dark-field lighting.
Figure 22B:
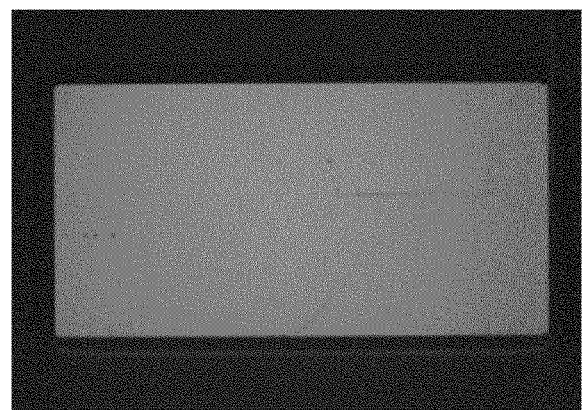
FIG. 22B is a digital image of a cracked surface illuminated via the imaging system using bright-field lighting.
Figure 22C:
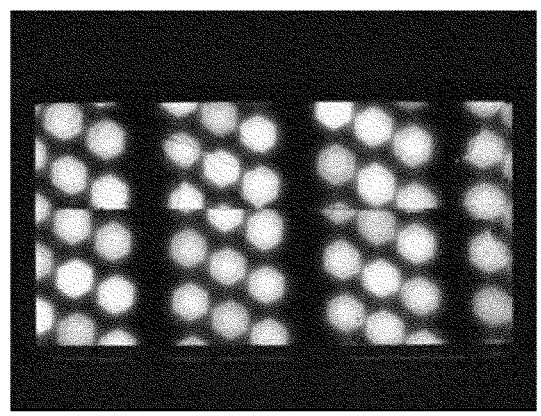
FIG. 22C is a digital image of a cracked surface illuminated via the imaging system using defocused light sources.

FIGS. 22A, 22B, and 22C show the same die with dark-field lighting, bright-field lighting, and defocused multiple-light-source lighting. The defocused light spots highlight the crack lines better than the other methods, as shown in FIG. 22C. Accordingly, in combination with the imaging system, a line detection algorithm may be used for purposes of automated crack detection by an image-processing computer.

Figure 23:
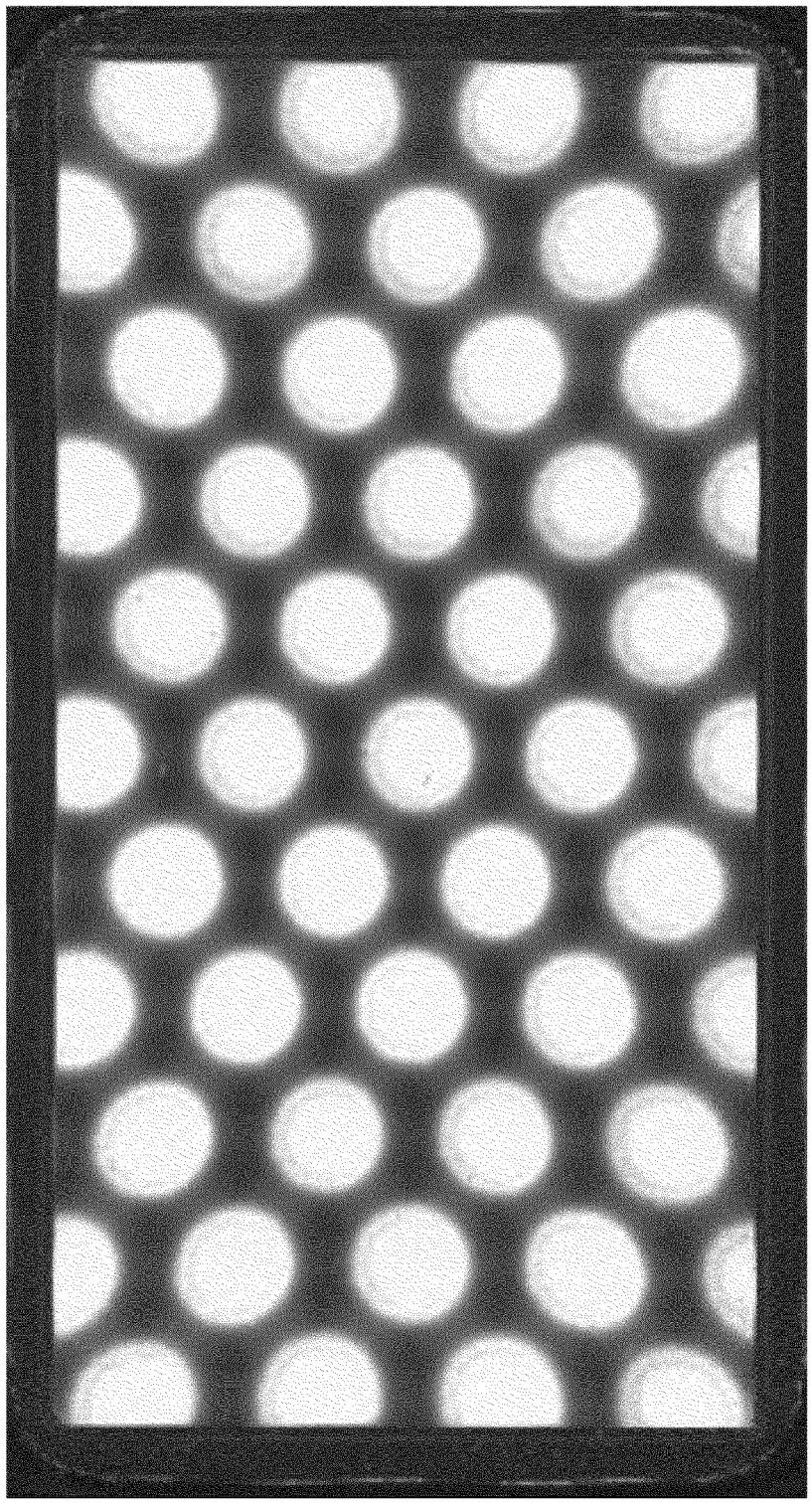
FIG. 23 is a digital image of a warped surface illuminated via the imaging system using defocused light sources.

If corners of a die are warped, circular light spots near the corners appear oval. Referring to FIG. 23, the reflected image of a die shows warping near corners of the die, where the spots are elongated (i.e., oval shaped). Such warping may be caused by attaching force or changes in thermal condition on the die. In general, by measuring the aspect ratio of the light spots, the presence and/or degree of warp may be measured.

VI. Alternate embodiment

In some contemplated embodiments, manual or automated inspection systems and methods described herein may be used for partially reflective surfaces that are not flat. The shapes of reflected light spots received by the image receiver may be compared to a reference set that corresponds to known curved shapes, such as precisely curved surfaces of a telescope mirror. Irregularities in the light spots of reflected spots may indicate defects in the curved surfaces.

In some contemplated embodiments, manual or automated inspection systems and methods described herein may be used for inspecting fine, complex geometries. In some such embodiments, the surfaces to be inspected may be precisely moved by on a slide or actuated table. As the surfaces move, the fine, complex geometries will reflect the light spots, which will move with respect to one another in repeating sequences. The repeatability of the sequence can be measured or observed, which may be indicative of the similarities of the complex surface geometry to another such surface.

While the reflected light forms light spots in some of the embodiments disclosed herein, in other embodiments, the reflected light may for other shapes, patterns, designs, etc. In contemplated embodiments, the reflected lights form grid lines that are received by the image receiver. In other contemplated embodiments, the reflected lights geometric shapes. The light spots may be any shape, depending upon particular embodiments. However, circular light spots are preferred in some embodiments because the shape of circular light spots is less dependent upon the orientation of the aperture.

VII. Advantages of Preferred Embodiments

In some embodiments, single light sources produce parallel line light spots. Such embodiments may result in different sensitivity in X- and Y-directions for crack detection. By contrast, in preferred embodiments, multiple light sources are used to create an array of circular light-spots, and sensitivities in X- and Y-directions are the same.

In some embodiments, aperture cropping may not be used. By contrast, in preferred embodiments, aperture cropping is used to reduce blurring and improve the efficiency of detection.

In some embodiments, one or more light spots produced by multiple light sources can be turned on and off, and each light spot may be turned brighter and dimmer than other light spots. As such, individual control of light spots may be used to detect light spots location and motion for surface tilt detection and for other purposes.

In some embodiments, any light spot can be moved closer or farther from any other light spots. Furthermore, movement of the array of light spots may magnify the appearance of surface defects without dependence on camera resolution.

The construction and arrangements of the imaging system, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A system for detecting crack, tilt, and warping of a reflective surface, comprising:
    an array of a plurality of light sources;
    a platform structure configured to hold the surface such that the surface is configured to receive light from the light sources;
    an image receiver configured to acquire an image that includes a plurality of individual reflected light spots;
    a lens aligned with the platform structure, wherein the lens is positioned such that the reflected light spots in the image are not in focus, but the surface is in focus;
    a cropping aperture configured to crop each reflected light spot in the image reflected from the surface,
    wherein the cropping aperture and the image receiver are configured such that each of the reflected light spots in the image have a shape that is defined by the cropping aperture.

2. The system of claim 1, wherein the cropping aperture is circular.

3. The system of claim 1,
    wherein the image receiver comprises an optical sensor configured to receive the reflected light spots via the lens, and
    wherein the system further comprises a computer in communication with the optical sensor, wherein the computer is configured to identify irregularities on the surface based upon distortions in the image of the reflected light spots acquired by the optical sensor.

4. The system of claim 3, further comprising a line-detection algorithm, wherein the computer uses the line-detection algorithm to process the image received by the optical sensor for indicia of cracks on the surface based on distortions in the image of the reflected light spots.

5. The system of claim 1, further comprising a beam splitter configured to receive light from the light sources and redirect the light toward the platform structure to be reflected by the surface, wherein the beam splitter is aligned with the lens and the platform structure.

6. The system of claim 5, wherein the beam splitter is configured to lengthen a light source working distance to magnify light spot distortions caused by flatness errors in the surface.

7. The system of claim 5, wherein the beam splitting lengthens a light source working distance to magnify light spot distortions caused by flatness errors in the surface.

8. The system of claim 1, further comprising a computer in communication with the array of light sources and the image receiver, wherein the computer is configured to operate some light sources differently than other light sources of the array to identify particular light sources received by the image receiver.

9. The system of claim 1, wherein the array of light sources comprises a symmetric arrangement.

10. The system of claim 1, wherein the system does not include a diffuser that smooths the light from the light sources, and the lens is configured such that the lack of focus of the light sources smooths the light spots in an image of the light spots imaged by the image receiver.

11. The system of claim 1, wherein the cropping aperture is located between the lens and the image receiver.

12. A system for detecting crack, tilt, and warping of a reflective surface, comprising:
an array of a plurality of light sources;
a platform structure configured to hold the surface such that the surface is configured to receive light from the light sources;
an image receiver configured to acquire an image that includes a plurality of individual reflected light spots;
a lens aligned with the platform structure, wherein the lens is positioned such that the reflected light spots in the image are not in focus, but the surface is in focus;
a circular cropping aperture configured to crop each reflected light spot in the image reflected from the surface; and
a beam splitter configured to receive light from the light sources and redirect the light toward the platform structure to be reflected by the surface, wherein the beam splitter is aligned with the lens and the platform structure,
wherein the cropping aperture and the image receiver are configured such that each of the reflected light spots in the image have a shape that is defined by the cropping aperture.

13. A method for detecting crack, tilt, and warping of a reflective surface, comprising:
directing light from an array of a plurality of lights to the surface;
focusing a lens on the surface for receiving light reflected from the surface;
cropping the reflected light received from the surface; and
examining an image produced from the cropped light for irregularities in a plurality of individual light spots associated with the reflected light, wherein the irregularities correspond to crack, tilt, and warping of the surface,
wherein the cropping is performed such that the image produced from the cropped light includes a plurality of individual light spots generated by individual ones of the plurality of light sources, each of the light spots having a shape that is defined by the cropping.

14. The method of claim 13, wherein the cropping is performed using a circular aperture.

15. The method of claim 13, wherein the examining step further comprises comparing the produced image with an image from a reference surface.

16. The method of claim 15, wherein the examining step further comprises processing the image produced with a computer and searching the image produced with a line-detection algorithm to identify indicia of cracks on the surface based on distortions in the image of the light spots.

17. The method of claim 13, wherein the directing step further comprises beam splitting the light from the array of lights.

18. The method of claim 17, wherein the directing step further comprises reflecting the light from the array of lights toward the surface.

19. A method of using an imaging system to inspect a surface for cracks, warping, and tilting, the method comprising:
recording size, shape, and position of a plurality of individual light spots reflected from a reference surface;
recording size, shape, and position of a plurality of individual light spots reflected from a surface to be inspected; and
comparing the size, shape, and position of the plurality of individual light spots reflected from the surface to be inspected with the size, shape, and position of the plurality of individual light spots reflected from the reference surface.

20. The method of claim 19, further comprising identifying individual sources of the light spots reflected form the surface to be inspected.

21. The method of claim 20, further comprising dimming or turning off one or more of the individual sources to distinguish the corresponding light spots from others of the light spots.

22. The method of claim 19, further comprising saving the size, shape, and position of the light spots reflected from the reference surface.

23. The method of claim 22, further comprising uploading the saved size, shape, and position of the light spots reflected from the reference surface during inspection of the surface to be inspected.

24. The method of claim 19, further comprising aligning an image of the light spots reflected from the surface to be inspected with an image of the light spots reflected from the reference surface.

25. The method of claim 19, wherein the size and shape of each light spot is controlled by a cropping aperture of an image receiver that records the size, shape, and position of the light spots reflected from the reference surface and the surface to be inspected.

26. The method of claim 25, wherein the cropping aperture is circular.

27. The method of claim 25, wherein each of the light spots has a shape defined by the cropping aperture.

28. The method of claim 19, further comprising measuring the size, shape, and position of at least some of the light spots reflected from the reference surface and the surface to be inspected.

29. The method of claim 19, further comprising defocusing on individual sources of the light spots reflected from the reference surface and the surface to be inspected.

30. The method of claim 19, wherein the comparing step does not use a predefined mathematical pattern of circles to compare with the size, shape, and position of light spots reflected from the surface to be inspected.

* * * * *